(12) United States Patent
Clark et al.

(10) Patent No.: US 6,433,187 B1
(45) Date of Patent: Aug. 13, 2002

(54) CERTAIN POLYCYCLIC COMPOUNDS USEFUL AS TUBULIN-BINDING AGENTS

(75) Inventors: David Clark, Albany; Walter Frankmoelle, South San Francisco; Jonathan Houze, San Mateo; Juan C. Jaen, Burlingame; Julio C. Medina, San Carlos, all of CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/464,217

(22) Filed: Dec. 15, 1999

Related U.S. Application Data

(60) Provisional application No. 60/112,613, filed on Dec. 17, 1998.

(51) Int. Cl.$^7$ ............... C07D 337/08; C07C 381/08; C07C 237/06
(52) U.S. Cl. ............... 549/12; 564/79; 564/166
(58) Field of Search ............... 552/625; 564/79, 564/166; 549/12

(56) References Cited

U.S. PATENT DOCUMENTS

| | | | |
|---|---|---|---|
| 4,087,429 A | 5/1978 | Katner et al. | 540/478 |
| 4,122,082 A | 10/1978 | Wright et al. | 540/478 |
| 4,206,221 A | 6/1980 | Miller et al. | 514/471 |
| 4,614,820 A | 9/1986 | Zee-Cheng et al. | 544/126 |
| 5,262,409 A | 11/1993 | Margolis et al. | 514/283 |

FOREIGN PATENT DOCUMENTS

| | | |
|---|---|---|
| WO | WO 92/15291 | 9/1992 |
| WO | WO 94/08041 | 4/1994 |
| WO | WO 96/11184 | 4/1996 |
| WO | WO 96/13494 | 5/1996 |

*Primary Examiner*—Alan L. Rotman
*Assistant Examiner*—Janet Coppins
(74) *Attorney, Agent, or Firm*—Townsend and Townsend and Crew LLP

(57) ABSTRACT

Derivatives of known tubulin-binding compounds are provided in which a (poly)fluorobenzene, a fluoropyridine, or a fluoronitrobenzene moiety is incorporated or added to the structure. These derivatives can be used as antimitotic agents and can be considered covalent modifiers of tubulin. The strategy developed for each of the compounds is to i) append a fluorinated electrophile (e.g., pentafluorophenyl-sulfonamido, 2-fluoropyridyl, or 3,5-dinitro-4-fluorophenyl) to an existing functional group in a natural product, ii) replace an aromatic ring in a natural product with a fluorinated electrophile, or iii) attach a fluorinated electrophile to an open valence in a portion of the molecule that will not interfere with recognition and binding to the tubulin site. Derivatives are provided based on colchicine, steganacin, podophyllotoxin, nocodazole, combretastatin, curacin A, vinblastine, vincristine, dolastatin, 2-methoxyestradiol, dihydroxy-pentamethoxyflavanone and others.

1 Claim, No Drawings

CERTAIN POLYCYCLIC COMPOUNDS USEFUL AS TUBULIN-BINDING AGENTS

RELATED APPLICATION

This application claims the benefit under Title 35, United States Code §119(e), of U.S. provisional application No. 60/112,613 filed Dec. 17, 1998. The contents of the foregoing provisional application are incorporated herein by reference.

FIELD OF THE INVENTION

The present invention relates to novel compounds that are capable of covalently modifying covalently modifying β-tubulin and acting as therapeutic and diagnostic agents, and acting as therapeutic and diagnostic agents.

BACKGROUND OF THE INVENTION

Microtubules are subcellular organelles located in most eukaryotic cells and are involved in a variety of cell functions including mitosis, intracellular movement, cell movement and maintenance of cell shape. Microtubule assembly involves polymerization of tubulin and additional construction with other components of the microtubule (referred to as "microtubule-associated proteins" or MAPs).

Tubulin itself consists of two 50 kDa subunits Tubulin itself consists of two 50 kDa subunits (α- and β-tubulin) which combine in a heterodimer. The heterodimer binds two molecules of guanosine triphosphate (GTP). One of the GTP molecules is tightly bound and cannot be removed without denaturing the heterodimer, while the other GTP molecule is freely exchangeable with other GTPs. This exchangeable GTP is believed to be involved in tubulin function. In particular, the tubulin heterodimer can combine in a head-to-tail arrangement in the presence of GTP to form a long protein fiber, known as a protofilament. These protofilaments can then group together to form a protein sheet which then curls into a tube-like structure known as a microtubule. Interference with this process of microtubule construction affects the downstream processes of mitosis and maintenance of cell shape.

Most of the naturally-occurring antimitotic agents have been shown to exert their effect by binding to tubulin, rather than MAPs or other proteins involved in mitosis. For example, tubulin is the biochemical target for several clinically useful anticancer drugs, including vincristine, vinblastine and paclitaxel. Another natural product, colchicine, was instrumental in the purification of tubulin as a result of its potent binding, with β-tubulin being the target for colchicine. Colchicine and other colchicine site agents bind at a site on β-tubulin that results in inhibition of a cross-link between cys-239 and cys-354 (wherein the numbering refers to the between cys-239 and cys-354 (wherein the numbering refers to the β2 isotype) by such non-specific divalent sulfhydryl reactive agents as N,N'-ethylenebis-iodoacetamide. However, simple alkylation of cys-239 does not appear to inhibit colchicine binding to tubulin.

In addition to colchicine, other natural products are known that bind at the colchicine site and inhibit microtubule assembly, for example, podophyllotoxin, steganacin and combretastatin. Still other agents bind to sites on tubulin referred to as the Vinca alkaloid site and the Rhizoxin/Maytansine site. However, none of the noted natural products are thought to operate by covalent modification of tubulin.

SUMMARY OF THE INVENTION

The present invention provides natural product derivatives as well as derivatives of known tubulin-binding compounds in which a (poly)fluorobenzene, a fluoropyridine, or a fluoronitrophenyl moiety is incorporated or added to the structure. These derivatives can be used as antimitotic agents and can be considered covalent modifiers of tubulin. The strategy developed for each of the compounds is to i) append a fluorinated electrophile (e.g., pentafluorophenylsulfonamido, 2-fluoropyridyl, or 3,5-dinitro-4-fluorophenyl) to an existing functional group in a natural product, ii) replace an aromatic ring in a natural product with a fluorinated electrophile, or iii) attach a fluorinated electrophile to an open valence in a portion of the molecule that will not interfere with recognition and binding to the tubulin site. Derivatives are provided based on colchicine, steganacin, podophyllotoxin, nocodazole, combretastatin, curacin A, vinblastine, vincristine, dolastatin, 2-methoxyestradiol, dihydroxy-pentamethoxyflavanone and others.

The present invention further provides pharmaceutical compositions containing the natural product derivatives as well as therapeutic and diagnostic methods using those compounds and compositions.

DETAILED DESCRIPTION OF THE INVENTION

Definitions

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The present invention provides a variety of agents capable of covalent attachment to tubulin. Accordingly, the compounds are particularly useful as antimitotic agents for the treatment of cancer. The compounds are derivatives of naturally-occurring antimitotic agents as well as other tubulin-interacting compounds. Briefly, the compounds can be described as antimitotic agents having, for example, a pentafluorophenyl-sulfonamide group ($C_6F_5$—$SO_2$—NH—), a 2-fluoropyridyl group, a nitrofluorophenyl group or a dinitrofluorophenyl group. In each instance, the reactive fluorinated aromatic moiety is introduced into the parent compound by replacing an existing portion of the parent (e.g., an aromatic ring or lactone), by attaching to an available reactive functional group (e.g., hydroxyl, amino, carboxylic acid and the like), or by attaching to an otherwise unfunctionalized portion of the molecule. Each of the reactive fluorinated aromatic moieties is capable of covalently modifying a cysteine thiol owing to the electrophilic nature of the fluoroaryl moiety and the leaving group character of the fluorine atom.

Derivatives of parent tubulin-interacting compounds are also described in which small portions of the parent compound are replaced with fragments of similar size that can increase the reactivity of the aromatic electrophile. For example, an ethylene group (—$CH_2CH_2$—) can be replaced with a sulfonamido moiety (—$SO_2NH$—) in those positions wherein the reactivity of an adjacent pentafluorophenyl or tetrafluorophenyl group can be enhanced. Additionally, any of the noted fluorinated romatic electrophiles can be attached to the remainder of the molecule via a connecting element that further enhances the reactivity of the fluorinated electrophile (e.g., a sulfonyl group or a carbonyl group).

The tubulin-interacting agents on which the following embodiments are based have been described in, for example, Jordan, et al., *Med. Res. Rev.* 18(4):259–296 (1998), Bai, et al., *J Biol. Chem.* 271(21):12639–12645 (1996), Hamel, *Med. Res. Rev.* 16(2):207–231 (1996), Sackett, *Pharmacol. Ther.* 59(2):163–228 (1993) and Luduena, et al., *Pharmac. Ther.* 49:133–152 (1991).

The present invention generally provides tubulin binding agents that selectively and covalently bind to tubulin. The agents are derivatives of compounds which non-covalently bind to the colchicine binding site, the vinca alkaloid binding site, or the rhizoxin/maytansine binding site of tubulin. Additionally, the derivatives are formed by the attachment of a fluorinated aromatic electrophile to the parent non-covalent compounds, or by the replacement of a portion of the parent compound with the fluorinated aromatic electrophile. As used herein, the term derivative is also meant to include those agents in which a fluorinated aromatic electrophile is attached to the parent compound via a linker, preferably a linker which increases the electrophilic character of the fluorinated aromatic electrophile. Still further, the term "derivative" is meant to include those compounds in which small portions of the parent compound are replaced with fragments of similar size that also serve to enhance the reactivity of the fluorinated aromatic electrophile.

In preferred embodiments, the fluorinated aromatic electrophile comprises a pentafluorophenyl, tetrafluorophenyl, 2-fluoropyridyl, dinitrofluorophenyl or fluoronitrophenyl group.

In other preferred embodiments, the agent is a derivative of a compound selected from the group consisting of colchicine, podophyllotoxin, combretastatin, nocodazole, stegnacin, dihydroxy-pentamethoxyflananone, 2-methoxyestradiol, vinblastine, vincristine, dolastatin, curacin A, etoposide, teniposide, sanguinarine, griseofulvin, cryptophycins or chelidonine.

The invention is better understood with reference to the following non-limiting embodiments.

Preferred Embodiments of the Invention

Colchicine Derivatives

Colchicine (i) binds to tubulin at a site, now termed "the colchicine binding site," proximately located near Cys-239 of tubulin. Although colchicine has been referred to as an irreversible inhibitor of tubulin assembly, the precise mechanism of its action is unknown. Inspection of colchicine's chemical structure does not suggest that it operates via covalent attachment to tubulin. In an effort to develop more effective inhibitors of tubulin assembly, the present invention provides derivatives of colchicine that are capable of covalently binding to nucleophilic residues in the colchicine binding site (e.g., Cys-239 or other cysteine thiol groups).

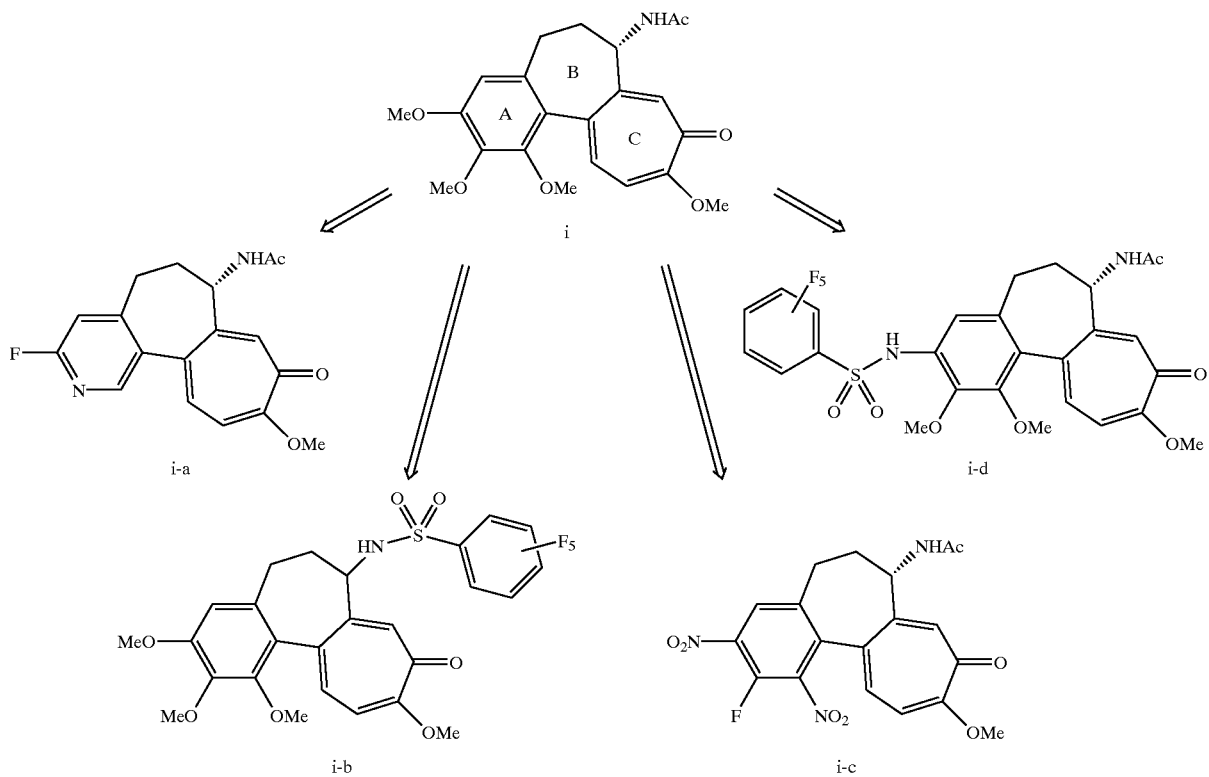

One group of embodiments is shown as i-a, in which the "A" ring of colchicine (the trimethoxybenzo group) has been replaced with a 2-fluoropyrido group. The 2-fluoropyrido group is known to be activated toward nucleophiles at the 2-position, ultimately resulting in displacement of the fluoro substituent. While i-a shows a 4,5-fused 2-fluoropyrido moiety, one of skill in the art will understand that ring fusion could also be at the 3,4 carbon bond or the 5,6 carbon bond and in either orientation. See, for example, the embodiments shown below as i-a[1] through i-a[5].

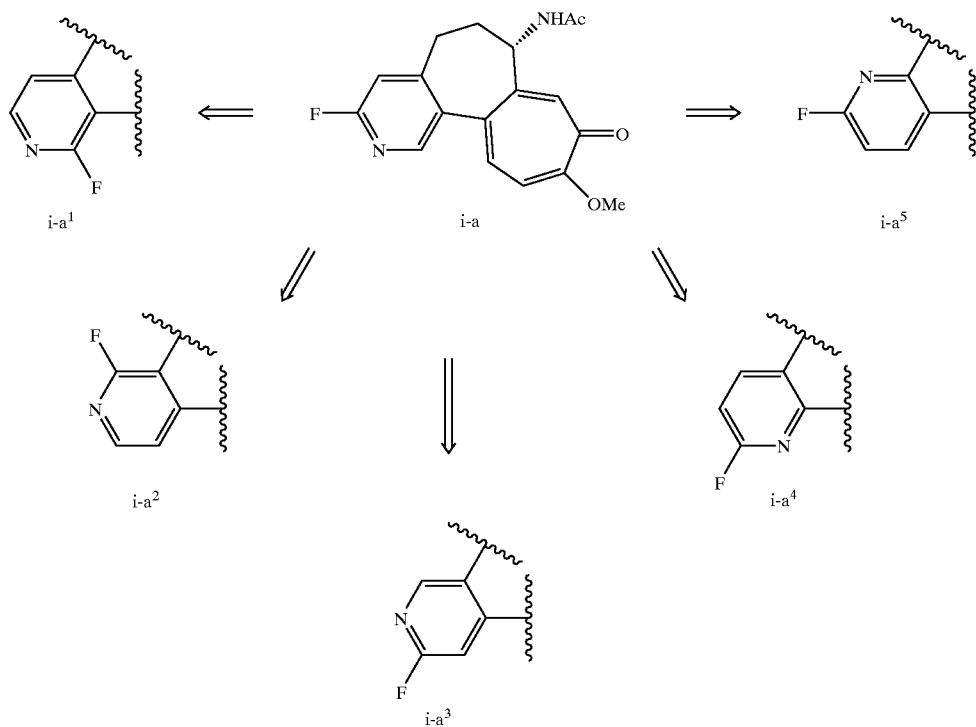

Another fused-ring replacement is shown above as i-c. In this group of embodiments, the "A" ring of colchicine has been replaced with a dinitrofluorobenzo group which also gives rise to multiple embodiments. For example, the dinitrofluorobenzo moiety can be fused to the "B" ring of colchicine (the cycloheptane ring) using either of two positional orientations to give rise to two compounds (shown as i-c and i-c$^3$). Additionally, the placement of the nitro groups can be altered such that they occupy positions ortho and para to the fluorine atom. In this orientation, the electron-withdrawing character of the nitro groups is very similar to the character imparted when they occupy the two positions which are ortho to the fluorine atom (see i-c$^1$ and i-c$^2$).

Additional embodiments involve the modification of functional groups already present on colchicine. For example, the acetamido group present in colchicine can be modified to contain a moiety capable of covalently attaching to a colchicine binding site nucleophile (see i-b). The pentafluorophenylsulfonyl group has been shown to be suitable for covalent attachment to Cys-239 of tubulin (see, WO 98/05315). In addition to the embodiment illustrated as i-b, the present invention provides other positional isomers in which the colchicine acetamido group is removed and a pentafluorophenylsulfonamido group is attached at any of the available valences (five additional valences) of the cycloheptane ring.

Still other embodiments are provided in which one of the methoxy groups of the colchicine "A" ring is replaced with a pentafluorophenylsulfonamido group (see, for example, i-d). One of skill in the art will understand that any of the methoxy groups can be replaced with the pentafluorophenylsulfonamido group (or an equivalent moiety for covalent attachment to tubulin). Still further, a pentafluorophenylsulfonamido group can be attached to the remaining open valence on the colchicine "A" ring, preferably with removal of the adjacent methoxy group.

Podophyllotoxin

Podophyllotoxin (ii) is an antimitotic agent that was first isolated from plants about 100 years ago, and more recently has been shown to exert its effects by binding to tubulin at the colchicine binding site. Interestingly, a computer modeling study suggests that there is an incomplete overlap between the colchicine binding site and the site occupied by podophyllotoxin, with the two trimethoxybenzene rings not binding in equivalent sites. Additionally, podophyllotoxin binding to tubulin is more rapid and reversible than the binding of colchicine. New derivatives are provided in the present invention which are designed to correct the deficiency of reversible binding.

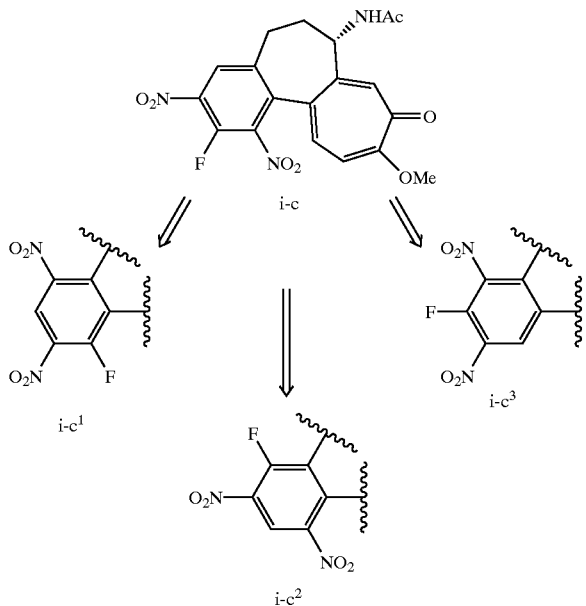

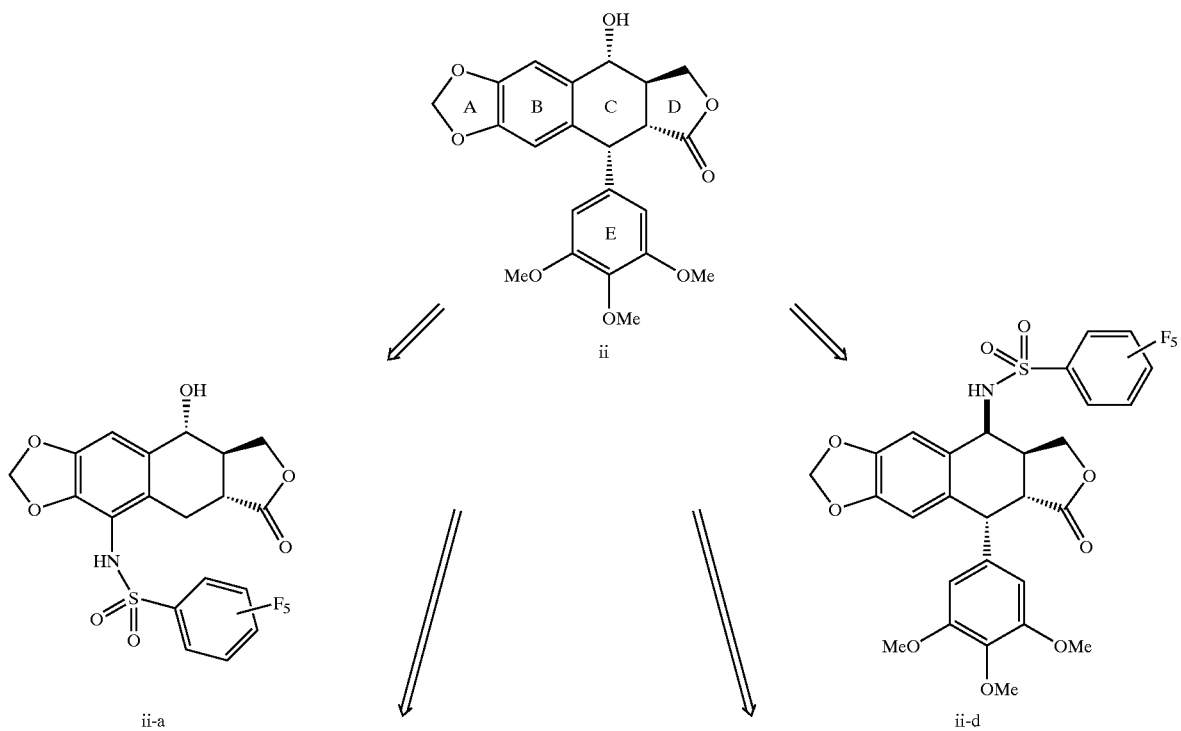

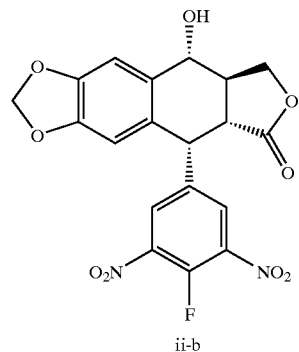

ii-b

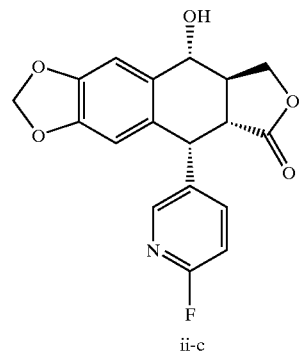

ii-c

In a first group of embodiments, the podophyllotoxin "E" ring (the trimethoxyphenyl ring) is removed and a pentafluorophenylsulfonamido group is attached to the "B" ring (see ii-a) to provide an electrophilic fluorinated aromatic ring in the approximate position of the removed "E" ring.

In other embodiments, the "E" ring is replaced with either a dinitrofluorophenyl moiety (e.g., ii-b) or a 2-fluoropyridyl moiety (e.g., ii-c). Positional isomers of ii-b and ii-c are also contemplated by the present invention. Thus, for either group of embodiments, attachment of the electrophilic aromatic ring can be through any available valence. Preferably, attachment is through a position that renders the fluorine most available for displacement by a binding site nucleophile.

In still other embodiments, the podophyllotoxin hydroxyl group (attached to the "C" ring) is replaced by a group suitable for covalent attachment to tubulin (e.g., a pentafluorophenylsulfonamido group, see ii-d).

Combretastatin

The combretastatins are another group of plant-derived antimitotic agents. First isolated and characterized in the early 1980's, the combretastatins (of which combretastatin A-4 (iii) is one of the most potent members) have been shown to bind to tubulin in a competitive manner to colchicine. Additional evidence has shown that the combretastatins bind rapidly and reversibly to tubulin.

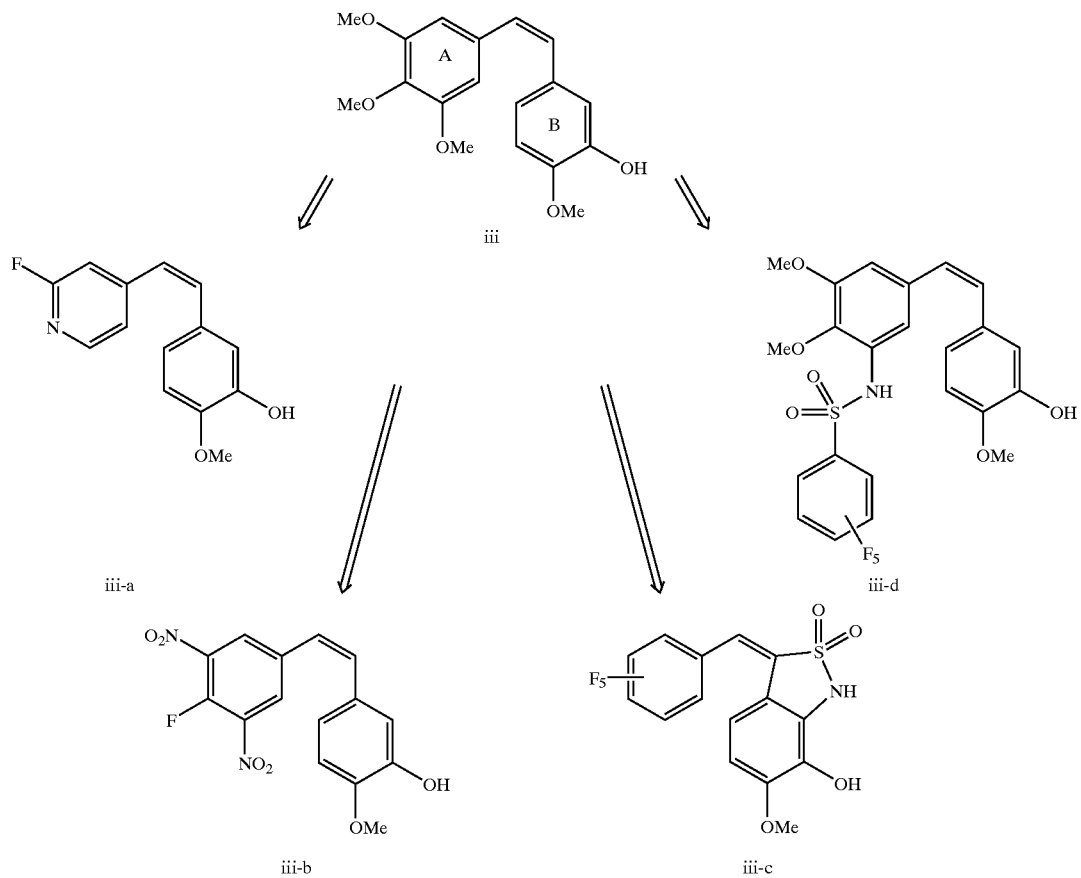

Incorporation of a covalent binding moiety into the combretastatin molecule is illustrated with compounds iii-a through iii-d. Compounds iii-a and iii-b exemplify the approach in which the trimethoxyphenyl (or "A") ring of combretastatin A-4 is replaced with a fluorinated electrophile group such as 2-fluoropyridyl and 3,5-dinitro-4-fluorophenyl. In each case, the point of attachment to the remainder of the molecule can be at the indicated position or at any other open valence of the fluorinated aromatic ring.

Similarly, the "A" ring of combretastatin can be replaced with a pentafluorophenyl group as indicated in iii-c. To further enhance the electrophilicity of the fluorinated aromatic ring, a sulfonamide bridging group (—$SO_2NH$—) is added to effectively form a vinylous pentafluorophenyl sulfonamido group.

In yet another group of embodiments, one of the methoxy groups of the combretastatin "A" ring can be replaced with a pentafluorophenylsulfonamido group (see, for example, iii-d). One of skill in the art will understand that any of the methoxy groups can be replaced with the pentafluorophenylsulfonamido group (or an equivalent moiety for covalent attachment to tubulin). Still further, a pentafluorophenylsulfonamido group can be attached to the remaining open valence on the combretastatin "A" ring, preferably with removal of the adjacent methoxy group.

The above modifications to combretastatin have been designed, developed and are illustrated with reference to the "A" ring of combretastatin. The present invention, however, is not so limited and provides additional embodiments in which similar modifications are carried out on the combretastatin "B" ring.

Nocodazole

Nocodazole (iv) was discovered as part of an antiparasitic program. Nocodazole and related benzimidazole derivatives have been shown to be competitive inhibitors of colchicine binding to tubulin. Some have postulated that the phenyl ring of iv binds to the same pocket of tubulin as the trimethoxyphenyl ring of colchincine.

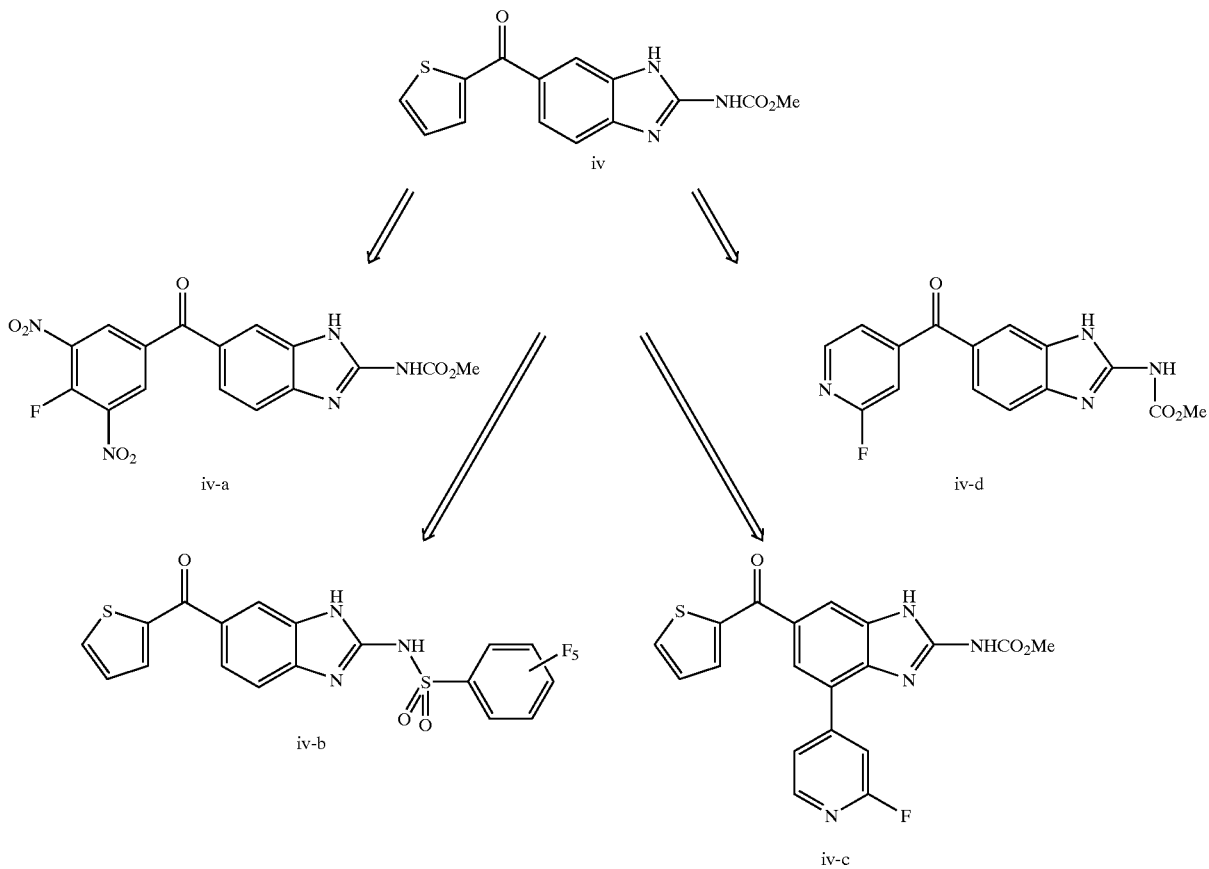

In one group of embodiments, the thienyl moiety of nocodazole is replaced with an electrophilic fluorinated aryl or heteroaryl moiety (see, for example, iv-a and iv-d). As with the other embodiments using fluorinated aryl or heteroaryl moieties, the point of attachment to the remainder of the molecule can be at any available valence on the aromatic ring. Additionally, the aryl group shown in iv-a as a 3,5-dinitro-4-fluorophenyl group can be substituted with the electronically similar 3,5-dinitro-2-fluorophenyl group and its equivalents (see, for example, isomers iv-a$^1$ through iv-a$^4$).

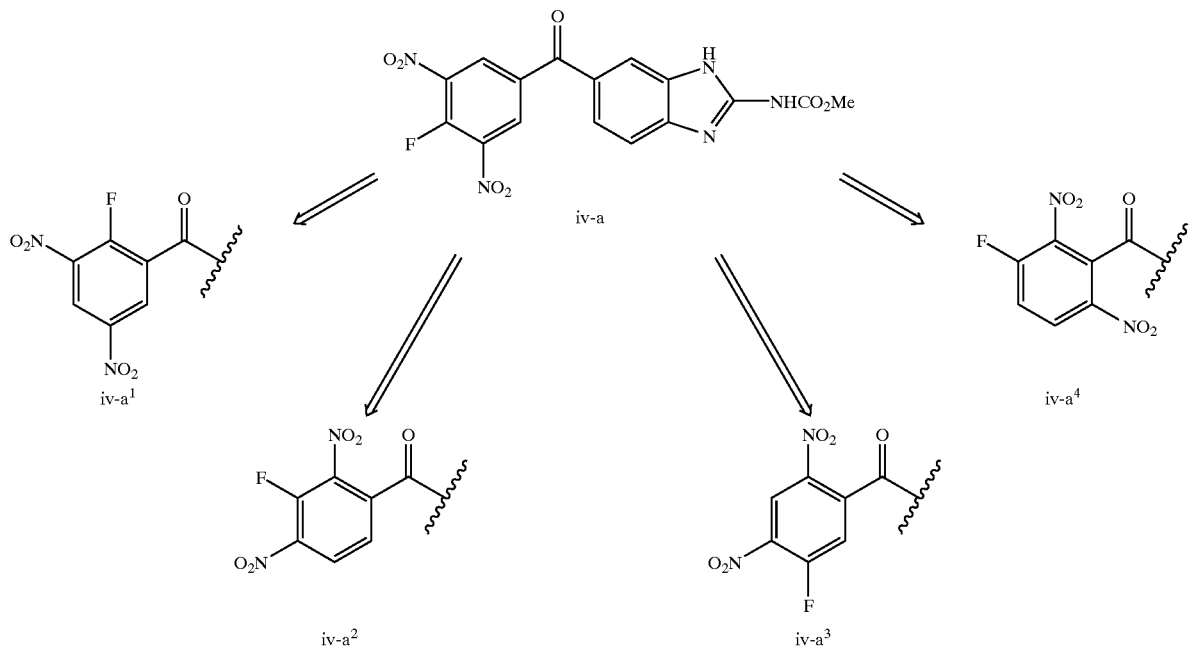

In another group of embodiments, the methyl carbamate present on the benzimidazole portion of nocodazole is replaced with a pentafluorophenylsulfonamido moiety (see iv-b). One of skill in the art will appreciate that other electrophilic aryl groups could be substituted for the pentafluorophenyl group, for example, a 3-nitro-4-fluorophenyl group.

In still other embodiments, nocodazole is modified to include an electrophilic fluorinated aryl or heteroaryl moiety at an open valence on the parent molecule (see, for example, iv-c).

2-Methoxyestradiol

In yet another group of embodiments, compounds are provided that are related to 2-methoxyestradiol (v).

Recently, 2-methoxyestradiol has been shown to be a weak competitive inhibitor of the binding of colchicine to tubulin and also inhibits the rate, but not the extent of tubulin assembly. Additional studies showed that rapid binding of 2-methoxyestradiol to unpolymerized tubulin could be inhibited with colchicine and other colchicine site agents. Still further work indicated that 2-methoxyestradiol binds to polymerized tubulin and that the altered properties of polymer formed in the presence of the agent may be due to this post-polymerization binding. Regardless of the precise mechanism of action, the compounds provided herein are capable of covalently modifying either tubulin itself or polymerized tubulin to modulate microtubule assembly.

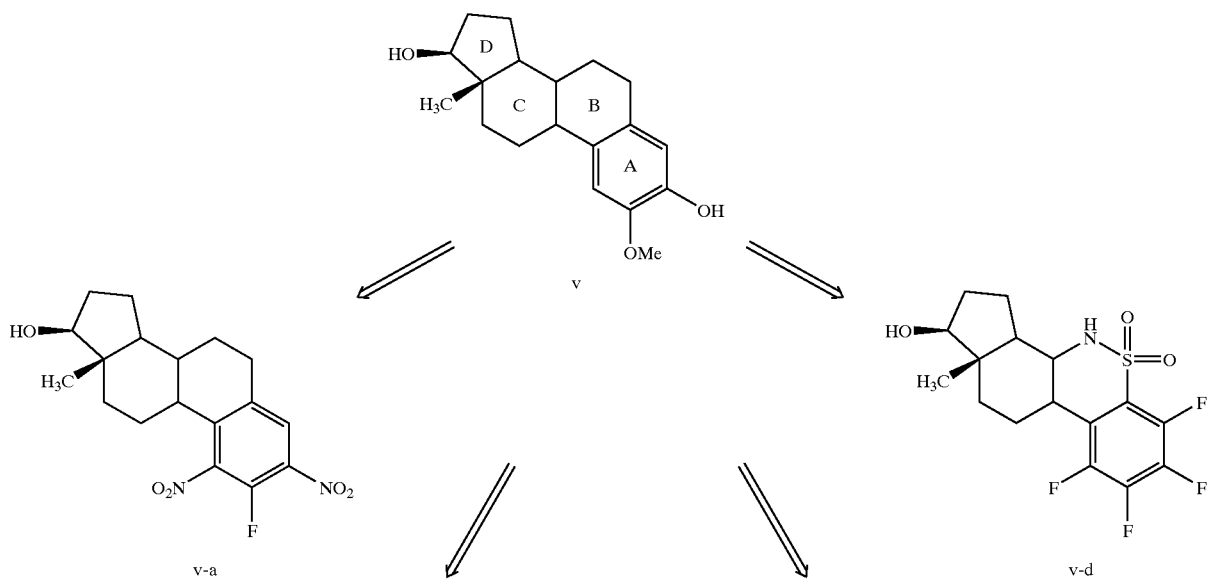

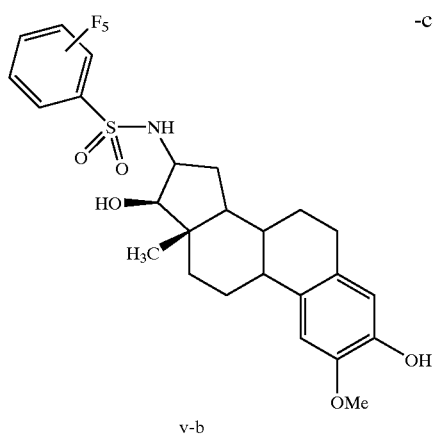

v-b

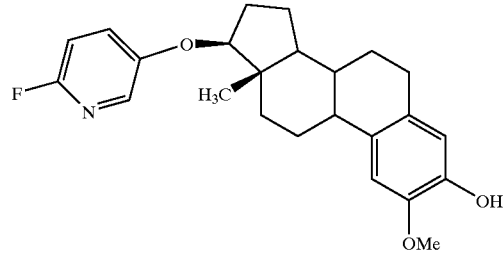

v-c

Application of the general design strategies, provided in other embodiments above, to 2-methoxyestradiol provides, for example, compounds v-a through v-d. In compound v-a, the aromatic ring of 2-methoxyestradiol is replaced with a dinitrofluorobenzene ring. Similarly, a 2-fluoropyridine ring could be substituted for the dinitrofluorobenzene ring to form additional compounds. For each of these two groups of fused-ring substitutions, positional embodiments similar to those described for i-a and i-c are also within the scope of the present invention.

Further embodiments are exemplified by compound v-b. As shown, compound v-b contains the entire steroid structure of 2-methoxyestradiol with an appended pentafluorophenylsulfonamido group attached at a position adjacent to the "D" ring hydroxy group. Attachment can also be carried out at any other position which can be readily functionalized by well-known methods in the steroid literature.

Addition of a 2-fluoropyridyl moiety to the estradiol nucleus constitutes yet another embodiment of the present invention (see, for example, v-c).

Finally, replacement of the aromatic ring and two "B" ring carbon atoms with a tetrafluorophenylsulfonamido moiety results in v-d.

Dihydroxy-pentamethoxyflavanone

Flavonol 2 (vi) is yet another compound isolated from higher plants which has been shown to be moderately cytotoxic and inhibit tubulin polymerization as well as the binding of colchicine to tubulin.

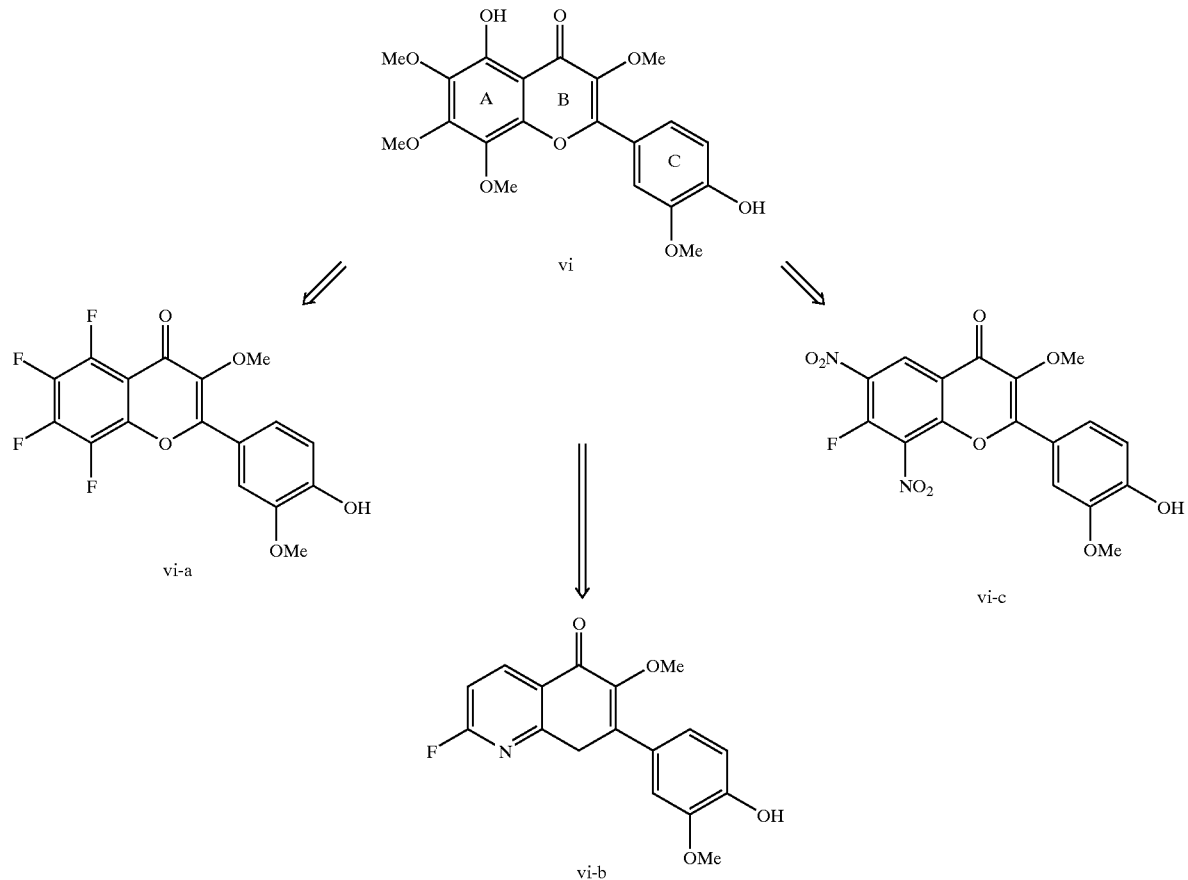

Compounds vi-a through vi-c illustrate that portion of the present invention in which the fused trimethoxyphenol (the "A" ring) is replaced with a tetrafluorobenzo group (vi-a), a 2-fluoropyrido group (vi-b) or a fluoronitrobenzo group (vi-c). In the case of the latter two compounds, positional isomers in which ring fusion occurs at other linkages on the electrophilic aromatic ring are also part of the present invention. In still other embodiments, the present invention provides those compounds and compositions in which the guaiacol group is replaced by a pentafluorophenyl, 2-fluoropyridyl, or a nitrofluorophenyl substituent.

Steganacin

Steganacin (vii) and a number of related compounds were initially isolated from the stems and stem bark of the East African tree Steganotaenia araliacea in the early 1970s. Steganacin shows significant similarity to both colchicine and podophyllotoxin. Accordingly, the strategies used to develop compounds derived from each of those natural products can be similarly applied to steganacin.

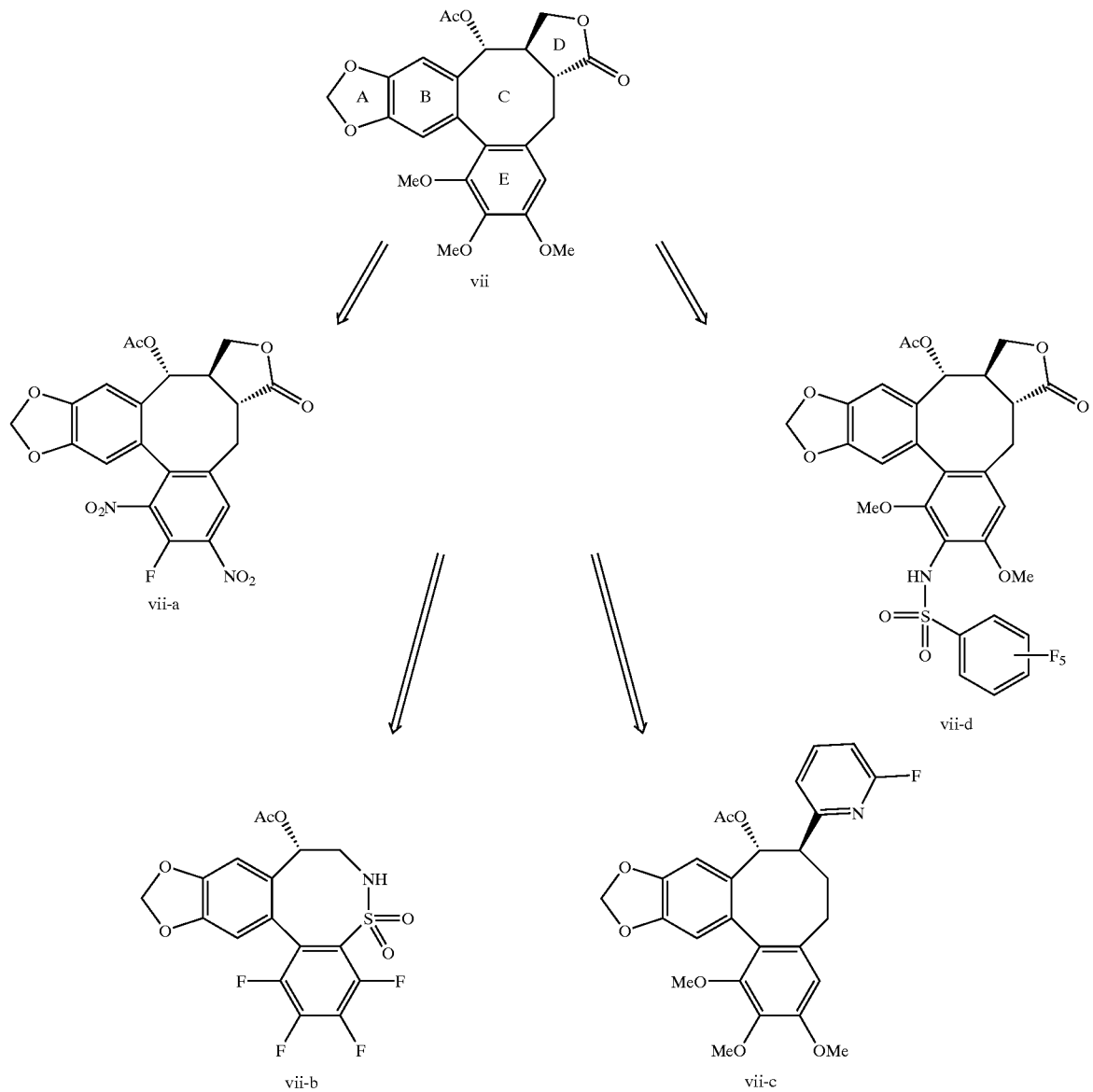

In a first group of embodiments, the trimethoxybenzo moiety of steganacin is replaced with a fluoronitrobenzo group. Compound vii-a shows one isomeric embodiment. The present invention also contemplates those embodiments in which the fused 1,3-benzodioxole group is similarly replaced with a 2-fluoropyrido or nitrofluorobenzo group.

In another group of embodiments, the trimethoxybenzo moiety of steganacin is replaced with a tetrafluorobenzo group, while two carbons of the cyclooctane ring are replace with a sulfonamide linkage to provide additional activation toward nucleophilic substitution on the fluorinated aromatic ring (see vii-b).

In yet another group of embodiments, the reactive lactone of steganacin is replaced by a covalent attaching group (e.g., 2-fluoropyridyl) to provide compounds such as vii-c In still other embodiments, a functional group can be removed and replaced with a covalent attaching group as exemplified in vii-d. Here, a methoxy group on the trimethoxybenzo portion of steganacin has been replaced by a pentafluorophenylsulfonamido moiety.

2-Phenyl-4-Quinolones

2-Phenyl-4-quinolones (exemplified by 6-(1-pyrolidinyl)-2-(3-methoxyphenyl)-4-quinolone (viii)) have been shown to be potent inhibitors of tubulin polymerization, and can arrest cell growth in a number of human tumor cell lines.

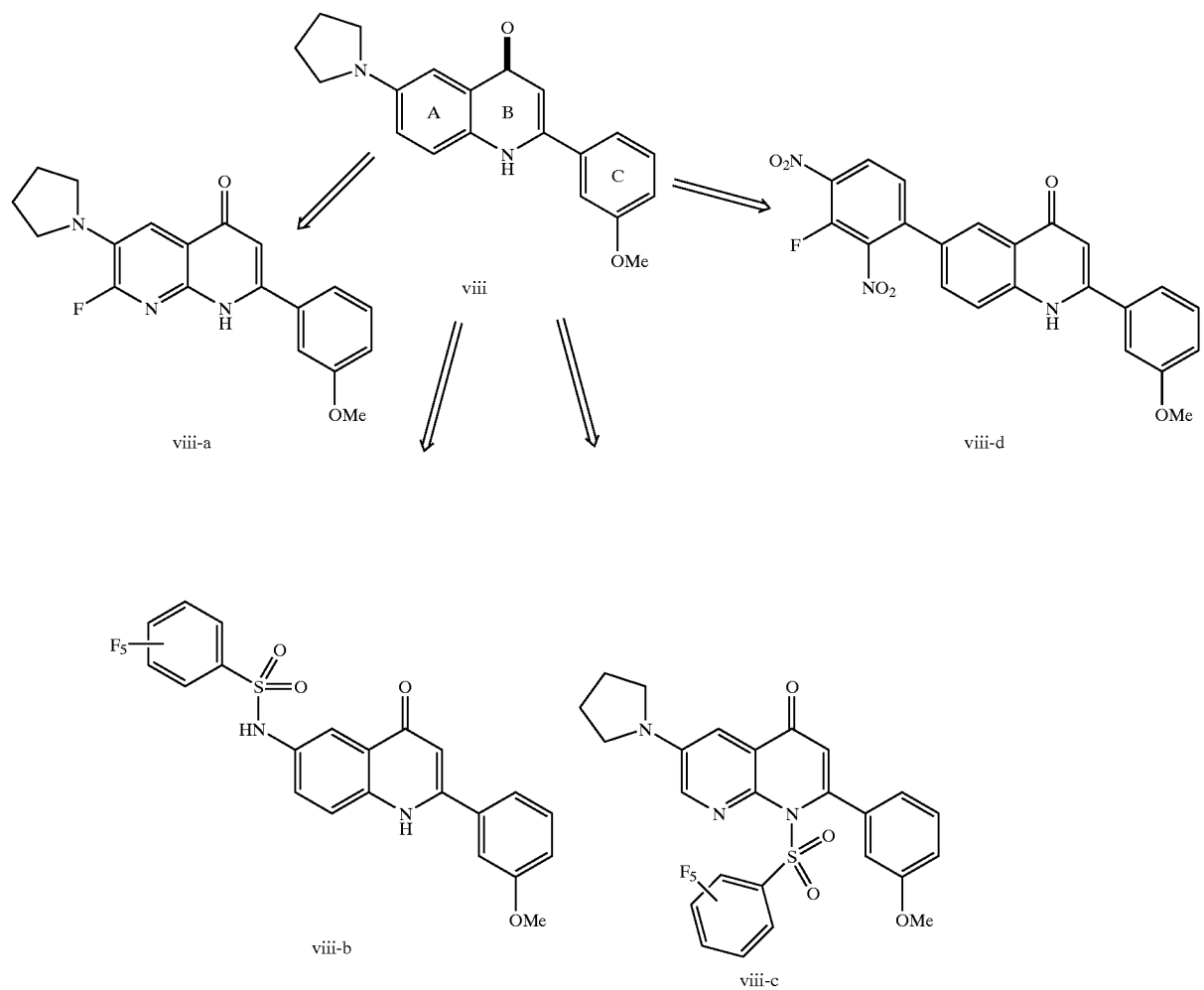

In one group of embodiments, the "A" ring of viii is replaced with a fluoropyridine ring (see viii-a). In other embodiments, an electrophilic fluorinated aryl moiety (e.g., pentafluorophenylsulfonyl) is attached to the quinolone nitrogen or to a nitrogen atom attached to the 6-position of the quinolone. In still other embodiments, the pyrolidinyl moiety of viii is replaced with, for example, dinitrofluorophenyl (see, viii-d).

ER-34410

ER-34410 (ix) is an antitumor agent first described in WO 95/03279. The compound was shown to have an $IC_{50}$ of 0.11 (g/mL against KB cells (human nasal cavity cancer) and is thought to bind noncovalently to the colchicine-binding site of tubulin.

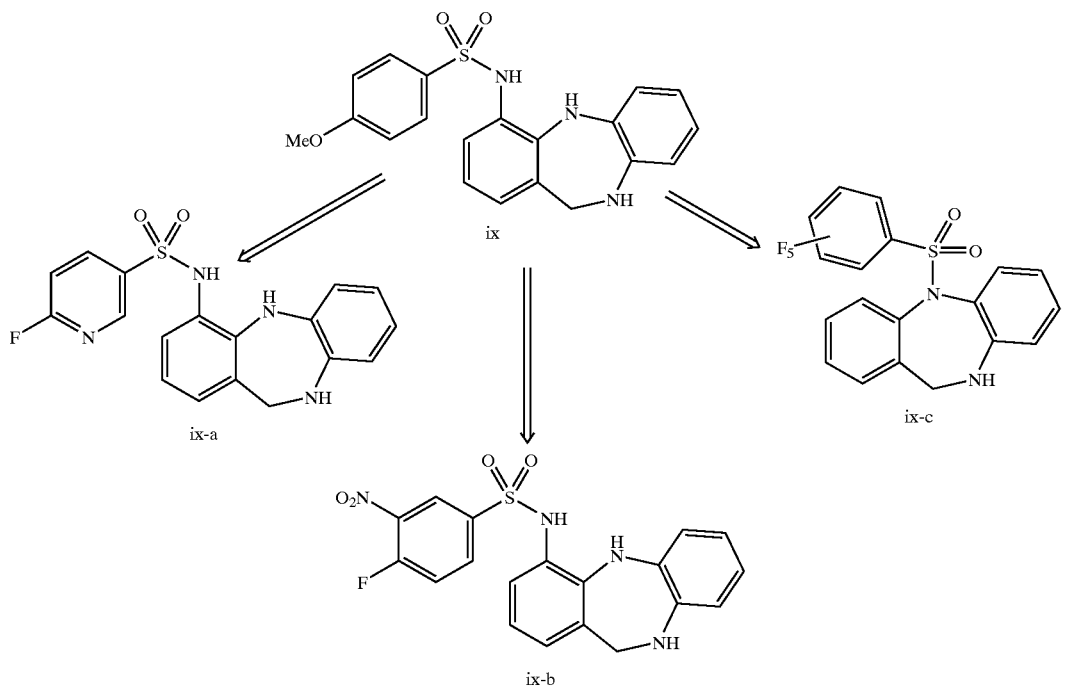

In one group of embodiments, the anisole ring of ER-34410 is removed and replaced with an electrophilic fluorinated aryl or heteroaryl group such as, for example, a 2-fluoropyridyl group (ix-a, shown attached through the 5-position of the pyridine ring), or a fluoronitrophenyl group (ix-b, shown attached through a position para to the fluorine atom).

In other embodiments, the entire 4-methoxyphenylsulfonamido group of ix can be removed and a pentafluorophenylsulfonyl group can be attached to either of the remaining nitrogens (those present in the 7-membered ring, to provide, for example, ix-c).

Vinblastine

Vinblastine (x), one of the Vinca alkaloids, has been used in the treatment of neoplastic diseases for several decades. While its antimitotic properties have been known almost since its discovery, the precise mechanism by which vinblastine achieves such disruption is less well understood.

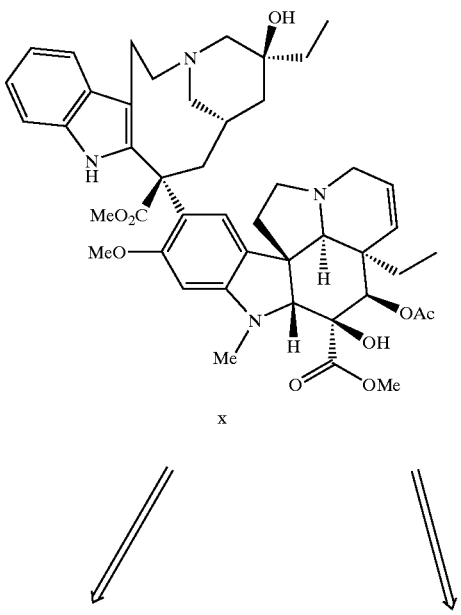

23

-continued

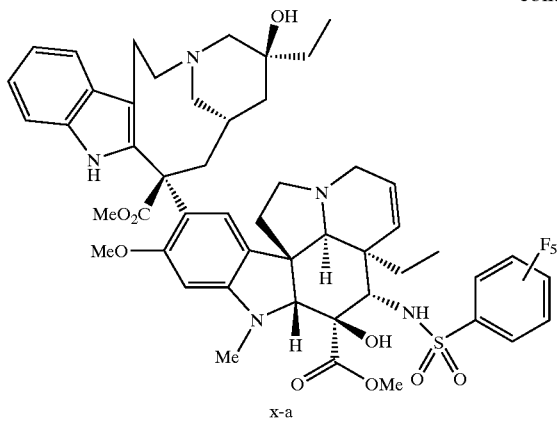

x-a

24

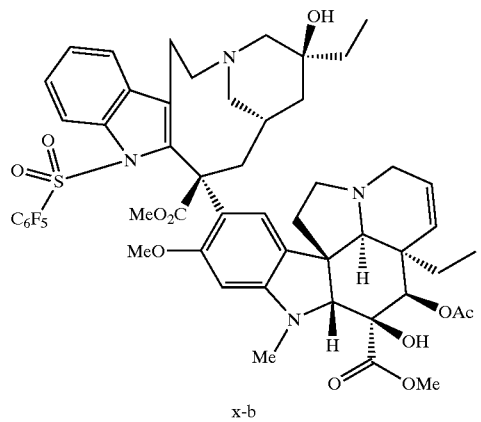

x-b

In one group of embodiments, the acetate functional group of vinblastine (x) is replaced by, for example, a pentafluorophenylsulfonamido group (see, x-a). In other embodiments, a pentafluorophenylsulfonyl group (or similar electrophilic moiety) is attached to the secondary indole nitrogen atom (see, x-b).

General Synthesis

In general, the compounds provided herein can be prepared using well-developed methodology for manipulation of functional groups on the parent compounds, or by modifications of synthetic methods used in the total synthesis of the parent natural products. For example, deacetylcolchicine (described by Lebeau, et al., *Synth. Commun.* 27:293–296 (1997)) can be sulfonylated with commercially available agents such as pentafluorophenylsulfonylchloride to produce i-b. Other synthesis methods are provided in the Examples.

Analysis of compounds

The compounds and compositions of the present invention exert their cytotoxic effects by interacting with cellular tubulin in a manner that is believed to be covalent and irreversible. Compounds and compositions may be evaluated in vitro for their ability to inhibit cell growth, for example, as described in Ahmed et al. (*J Immunol. Methods* 1994, 170, 211). Established animal models to evaluate antiproliferative effects of compounds are also known in the art. For example, compounds can be evaluated for their ability to inhibit the growth of human tumors grafted into immunodeficient mice using methodology similar to that described by Rygaard and Povlsen (*Acta Pathol. Microbiol. Scand.* 1969, 77, 758) and Giovanella and Fogh (*Adv. Cancer Res.* 1985, 44, 69).

Formulation and Administration of Compounds and Pharmaceutical Compositions

The invention provides methods of using the subject compounds and compositions to treat disease or provide medicinal prophylaxis by slowing and/or reducing the growth of tumors, etc. These methods generally involve contacting the cell with or administering to the host an effective amount of the subject compounds or pharmaceutically acceptable compositions. The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other antiproliferative therapeutic agents, different from the subject compounds. In many instances, administration in conjunction with the subject compositions will enhance the efficacy of such agents. Exemplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof.

The compounds and compositions also find use in a variety of in vitro and in vivo assays, including diagnostic assays. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples provide more detailed descriptions of synthetic methods used to prepare compounds of the present invention. One of skill in the art will appreciate that many of the methods provided below are applicable to the modification or derivatization of other known noncovalent tubulin-binding agents. Accordingly, the examples are offered by way of illustration and not by way of limitation.

EXAMPLES

Example 1

This example illustrates a method useful for the preparation of colchicine derivative i-b.

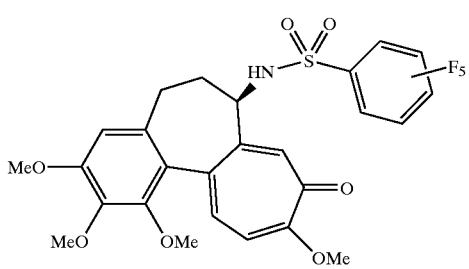

A solution of deacetylcolchicine (3.57 g; 0.01 mole; described by L. Lebeau et al., *Synth. Commun.*, 27:293–296 (1997)) and diisopropylethylamine (1.92 g; 0.014 mole) in dichloromethane (50 mL) is treated with pentafluorophenylsulfonyl chloride (3.19 g; 0.012 mole; available from Aldrich) while the reaction flask is cooled in an ice bath. The reaction mixture is then stirred at room temperature for 12 hours. Saturated sodium bicarbonate solution (50 mL) is added, followed by washing with brine, and drying ($MgSO_4$). After evaporation of the solvent in-vacuo, the crude reaction mixture is purified by column chromatography (silica; EtOAc:hexanes) to yield the title product.

Example 2

This example illustrates the preparation of podophyllotoxin derivative

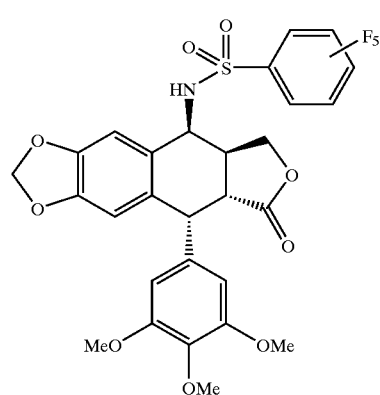

Diethyl azodicarboxylate (2.4 ml; 0.012 mole) is added dropwise to a solution of podophyllotoxin (4.14 g; 0.01 mole; available from Oclassen Pharmaceuticals Inc, San Rafael, Calif., under the trade name Condylox), pentafluorophenylsulfonamide (2.47 g; 0.01 mole; prepared by treatment of pentafluorosulfonyl chloride with conc ammonium hydroxide in dichloromethane, in an ice bath), and triphenylphosphine (2.7 g; 0.01 mole) in tetrahydrofuran (50 mL). The reaction mixture is stirred at room temperature until the alcohol group of podophyllotoxin has completely reacted (about 24 hours). Following evaporation of the solvent, the crude reaction product is purified by column chromatography (silica; $CH_2Cl_2$:MeOH) to yield the title product.

Example 3

This example illustrates the synthesis of vinblastine derivative x-b.

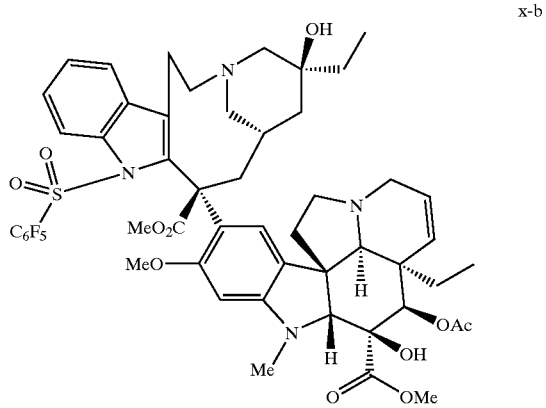

A solution of vinblastine sulfate (9.09 g; 0.01 mole; available from Sigma) and diisopropylethylamine (1.93 g; 0.015 mole) in anhydrous pyridine (100 mL) is cooled in an ice bath and treated dropwise with a solution of pentafluorophenylsulfonyl chloride (3.19 g; 0.012 mole; Aldrich) in dichloromethane (50 mL). The reaction mixture is stirred at room temperature for approximately 12 hours and is then treated with saturated sodium bicarbonate solution, washed with brine, and dried over $MgSO_4$. After evaporation of the dichloromethane, the crude residue is purified by column chromatography (silica gel, $CH_2Cl_2$:MeOH) to yield the title compound.

Example 4

This example illustrates the synthesis of vinblastine derivative x-a.

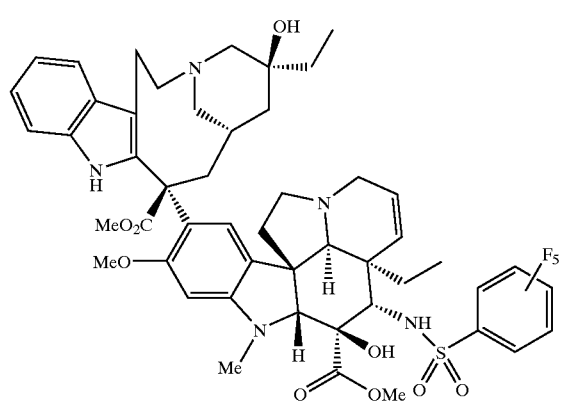

Vinblastine sulfate (9.09 g; 0.01 mole; available from Sigma) is dissolved in anhydrous methanol (100 mL) and treated with sodium methoxide (1.1 g; 0.02 mole). The resulting mixture is heated at reflux until the acetate group of vinblastine is hydrolized (about 12 hours). The methanol is evaporated in-vacuo, and the resulting crude product is purified by column chromatography (silica) or used directly in the next step.

Diethyl azodicarboxylate (2.4 ml; 0.012 mole) is added dropwise to a solution of the vinblastine alcohol obtained in the previous step ( 7.67 g; 0.01 mole), pentafluorophenylsulfonamide (2.47 g; 0.01 mole), and triphenylphosphine (2.7 g; 0.01 mole) in tetrahydrofuran (50 mL). The reaction mixture is refluxed for approximately 24 hours. Following evaporation of the solvent in-vacuo, the reaction mixture is purified by column chromatography (silica gel; $CH_2Cl_2$: MeOH) to yield the title compound.

Example 5

This example illustrates the synthesis of compound ix-b: 1-(4-fluoro-3-nitrophenylsulfonamido)-10H-phenothiazine

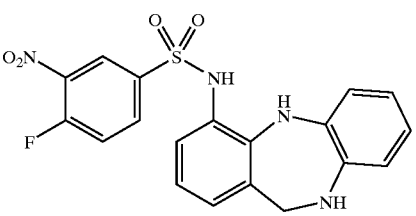

ix-b

A solution of 1-amino-10H-phenothiazine (2.11 g; 0.01 mole; prepared according to H. Yoshino et al., WO 94-JP1231 940726, see also Chemical Abstracts 122:314588) in anhydrous pyridine (10 mL) is treated dropwise with a solution of 4-fluoro-3-nitrobenzenesulfonyl chloride (2.07 g; 0.01 mole; prepared according to A. Courtin et al, *Helv. Chim. Acta* 66:68–75 (1983)) in tetrahydrofuran (5 mL), while the reaction flask is cooled in an ice bath. The reaction mixture is stirred at room temperature for about 12 hours until the reaction is complete (by TLC analysis). Following evaporation of the volatiles under vacuum, the residue is purified by column chromatography (silica gel; $CH_2Cl_2$: MeOH) to give the title compound.

Example 6

This example illustrates the synthesis of compound i-d.

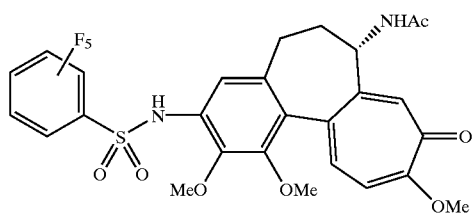

i-d 6.1 Preparation of Colchicine Triflate i-d²

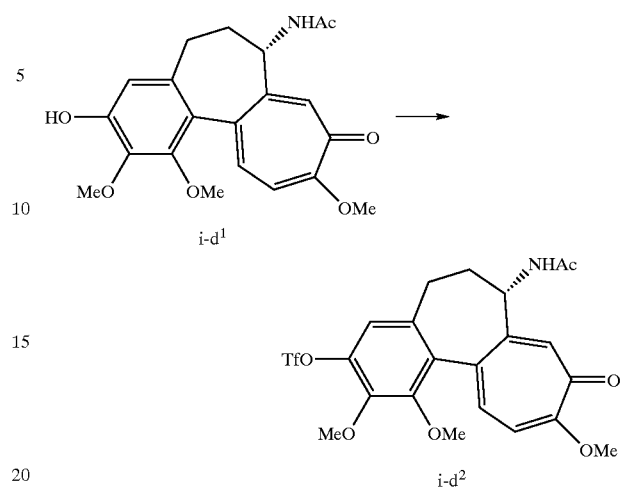

The aryl triflate i-d² is formed according to the method of Hendrickson and Bergeron (*Tetrahedron Lett.*, 4607–4610 (1973)). Briefly, a solution of 3-demethylcolchicine (3.85 g; 0.01 mole; described by M. Roesner, et al., *J Med. Chem.* 24:257–261 (1981)) and triethylamine (1.41 g; 0.014 mole) in dichloromethane (50 mL) at −78° C. is treated with phenyl triflimide (4.46 g; 0.0125 mole). The reaction mixture is stirred at −78° C. until TLC demonstrates complete consumption of the starting material. Saturated sodium bicarbonate solution (50 mL) is added, and the mixture is washed with brine, and dried ($MgSO_4$). Solvent is removed in-vacuo, and the crude reaction mixture is purified by column chromatography (silica; EtOAc:hexanes) to yield the title product.

6.2 Preparation of Colchicine Amine Derivative i-d³

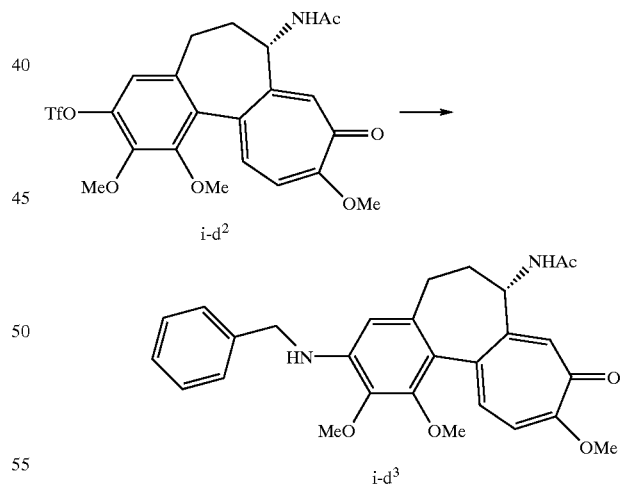

A palladium mediated coupling of benzylamine to aryl triflate i-d² is carried out according to the method of Buchwald (*J. Org. Chem.* 62:1264–1267 (1997)). Palladium acetate (40 mg, 0.18 mmol), BINAP (124 mg, 0.2 mmol), sodium tert-butoxide (1.21 g, 12.6 mmol), toluene (27 mL), and benzylamine (1.15 g, 10.8 mmol) are combined under an argon atmosphere then heated to 80° C. A solution of triflate i-d² (4.65 g; 9 mmol) in toluene (9 mL) is added dropwise over 30 minutes. The reaction mixture is stirred under argon at 80° C. until TLC demonstrates consumption of the starting material. After cooling, the reaction mixture is diluted with ether, filtered, concentrated under reduced pressure, and the residue is purified by column chromatography (silica; EtOAc:hexanes) to yield the title product.

6.3 Preparation of Colchicine Amine Derivative i-d⁴

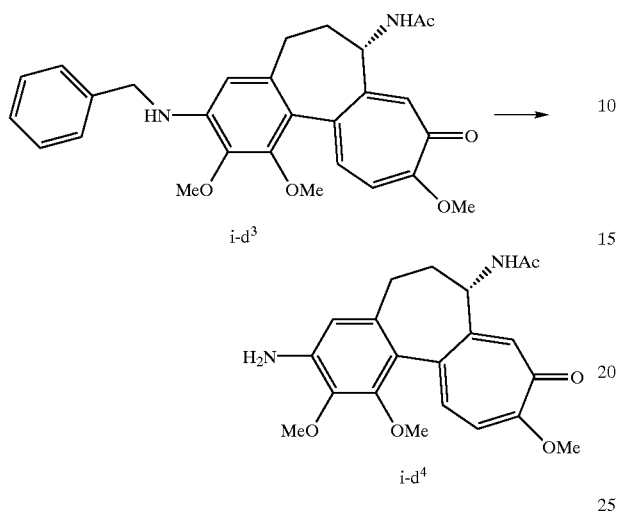

A solution of benzylamine i-d³ (2.84 g, 6 mmol) in 3N aqueous HCl (2.07 mL 6.2 mmol) and ethanol (20 mL) is hydrogenated (atmospheric pressure) over 10% Pd on C catalyst (50 mg). The reaction mixture is then stirred at room temperature until TLC demonstrates consumption of the starting material. After filtration to remove the catalyst, ethanol is removed from the filtrate under reduced pressure and the residue is poured into saturated sodium bicarbonate solution (50 ml). The aqueous solution is extracted twice with dichloromethane (50 mL). The mixture is washed with brine and dried (MgSO₄). After evaporation of the solvent in-vacuo, the crude reaction mixture is purified by column chromatography (silica; EtOAc: hexanes) to yield the title product.

6.4 Conversion of Amine Derivative i-d⁴ to Target i-d

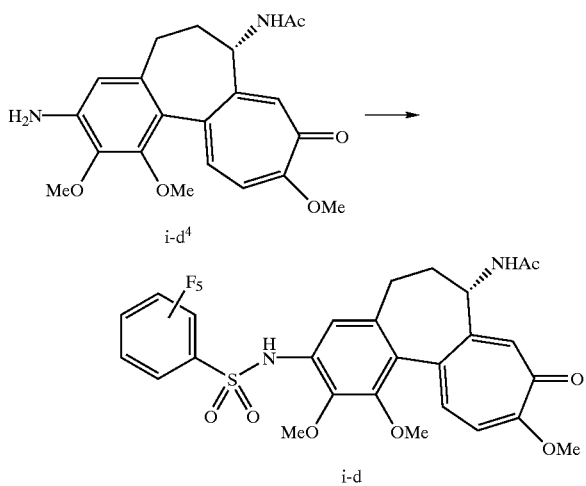

A solution of 3-des-methoxy-3-aminocolchicine (i-d⁴, 2.3 g; 6 mmol) and 2,6-lutidine (0.67 g; 6.3 mmol) in acetone (18 mL) is treated with pentafluorophenyl-sulfonyl chloride (1.68 g; 6.3 mmol) while the reaction flask is cooled in an ice bath. The reaction mixture is allowed to warm to room temperature and stirred until TLC demonstrates consumption of the starting material. The reaction mixture is filtered to remove 2,6-lutidine hydrochloride, concentrated in vacuo, and the residue purified by column chromatography (silica; EtOAc:hexanes) to yield the title product.

Example 7

This example illustrates the synthesis of compound ii-c.

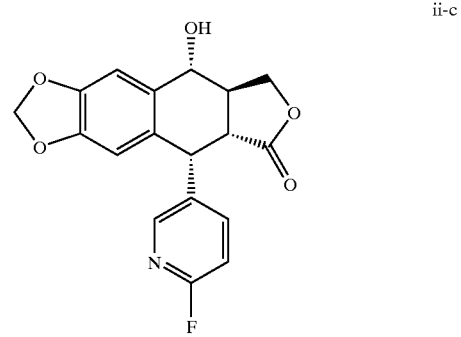

7.1 Preparation of Fluoropyridine Cuprate Reagent

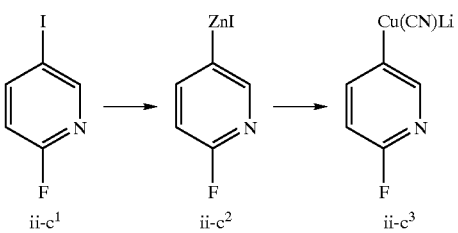

The formation and conjugate addition of the fluoropyridyl cuprate ii-c³ is carried out according to the method of Rieke (*J. Org. Chem.*, 56:1445 (1991)). Rieke zinc is prepared as described in the reference, and 2-fluoro-5-iodopyridine (1.5 g; 7 mmol; described by Liang, et al., *J Med Chem.* 40:2293–95 (1997)) is added neat to the active zinc (15.4 mmol). After stirring for three hours, the excess zinc is allowed to settle and the organozinc reagent cannulated into a second flask containing CuCN (0.65 g, 7.3 mmol) and anhydrous LiBr (1.27 g, 14.7 mmol) in anhydrous THF (10 mL) at −20° C. under argon. The solution is allowed to warm to 0° C., stirred for 15 minutes, and carried on directly.

7.2 Preparation of Precursor ii-c$^e$

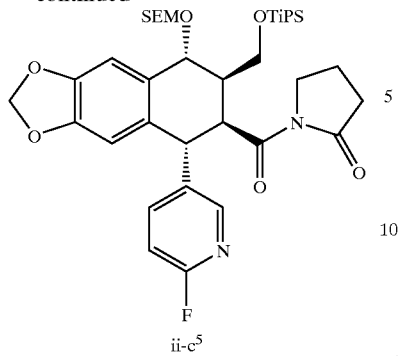

ii-c[5]

The reaction mixture from 7.1 above is cooled to −78° C. and TMS-Cl (1.44 g, 13.2 mmol) and BF₃·OEt₂ (1.6 g, 11.2 mmol) are added. After 15 minutes, a solution of enamide ii-c[4] (3.4 g, 5.6 mmol, described by Berkowitz, et al., *J Am. Chem. Soc.* 118:9426–27 (1996)) in THF (20 mL) is added and the reaction stirred at −78° C. for three hours. The reaction mixture is allowed to warm to 0° C. and is stirred until TLC demonstrates completion of the reaction. Saturated ammonium chloride solution (20 ml) is added, the layers separated, and the aqueous layer extracted with ether (3×20 mL). The combined organic layers are washed with saturated brine, and dried over MgSO₄. After evaporation of the solvent in-vacuo, the crude reaction mixture is purified by column chromatography (silica; EtOAc:hexanes).

7.3 Preparation of Podophyllotoxin Derivative ii-c

Transformation of ii-c[5] into the podophyllotoxin analog ii-c can be carried using the procedures described by Berkowitz, et al., *J Am. Chem. Soc.*, 118:9426–27 (1996).

Example 8

This example illustrates the synthesis of nocodazole derivative iv-b.

8.1 Preparation of nocodazole acid iv-b²

To a solution of nocodazole (iv, 301 mg, 1 mmol, Aldrich) in THF (1 mL), methanol (1 mL) and water (1 mL) is added lithium hydroxide (24 mg, 1 mmol). The reaction mixture is stirred at room temperature overnight and then treated with 1M NaOH (20 mL) and extracted with ethyl ether (2×15 mL). The water layer is acidified with 3M HCl (20 mL) and extracted with methylene chloride (3×20 mL). Drying (MgSO₄) followed by concentration yields the desired carboxylic acid.

8.2 Preparation of nocodazole amine derivative iv-b³

A solution of acid iv-b² (272 mg, 1 mmol) in toluene (22 mL) is treated with diphenyl phosphorazidate (0.25 mL, 1.2 mmol) and triethylamine (0.16 mL, 1.17 mmol). The mixture is heated to reflux for 6 hours, then treated with water (1 mL) and heated overnight. The reaction mixture is cooled to room temperature, treated with saturated NaHCO₃ (15 mL) and extracted with ethyl acetate (3×20 mL). The combined extracts are dried (K₂CO₃) and concentrated. Purification by column chromatography (silica gel; hexanes:EtOAc) yields the title product.

8.3 Conversion of iv-b³ to iv-b.

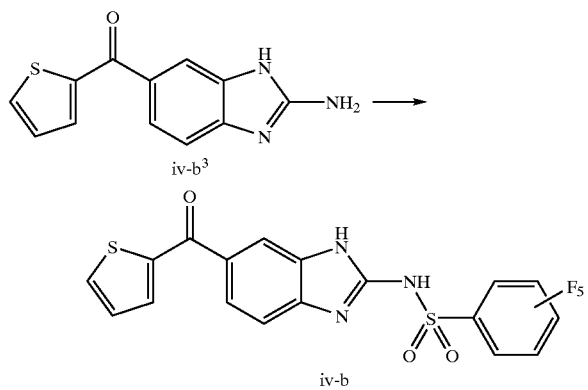

A solution of amine iv-b³ (243 mg, 1 mmol) and 2,6-lutidene (110 mg, 1.05 mmol) in acetone (3 mL) is treated with pentafluorophenylsulfonyl chloride (0.28 g, 1.05 mmol) while the reaction flask is cooled on an ice bath. The reaction mixture is allowed to warm to room temperature and stirred until TLC shows no starting material remains. The reaction mixture is filtered, concentrated and the residue purified by column chromatography (silica gel; hexanes:EtOAc) to obtain the product.

Example 9

This example illustrates the synthesis of compound iii-d.

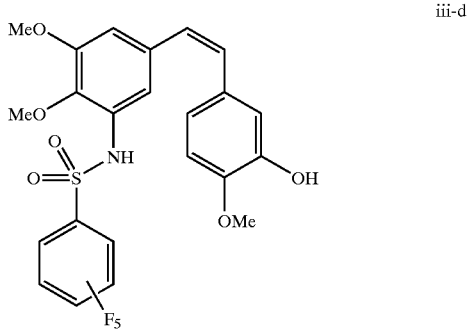

9. 1. Preparation of iii-d²

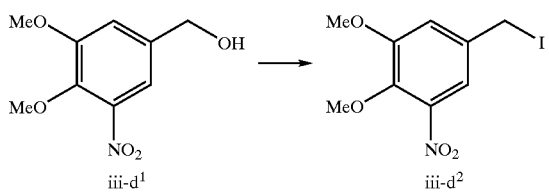

Benzyl alcohol iii-d¹ (681 mg, 3.2 mmol; previously described by Firnan, et al, *J Med Chem.*, 16:416 (1973)) is treated with triphenylphosphine (937 mg, 3.6 mmol) and imidazole (277 mg, 4.1 mmol). THF (5 mL) is added and the resulting solution cooled to 0° C. Iodine (1.10 g, 4.30 mmol) is added and the resulting solution stirred at 0° C. until TLC shows no starting material. At this time, saturated $Na_2S_2O_3$ (2 mL) is added and the mixture poured onto water and extracted with ether. The combined ether extracts are dried ($MgSO_4$) and concentrated. The residue is passed through a plug of silica gel eluting with ether to provide the desired product after concentration of the filtrate.

9.2 Preparation of phosphonium salt iii-d³

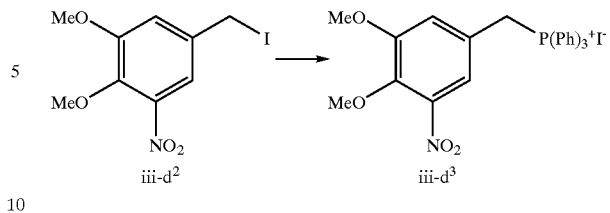

Iodide iii-d² (323 mg, 1 mmol) is diluted with benzene (5 mL) and triphenylphosphine (262 mg, 1 mmol) is added. The resulting solution is heated at 50° C. until no starting material remains as determined by TLC analysis. The mixture is cooled to 0° C. and the solid product collected by filtration.

9.3 Preparation of alkene iii-d⁵

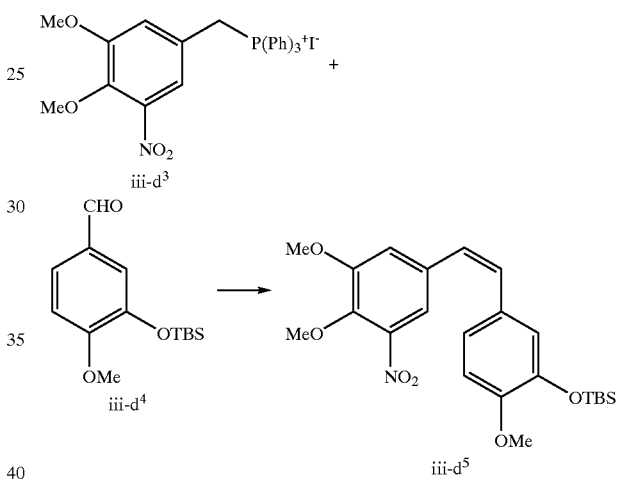

To a solution of iii-d³ (585 mg, 1 mmol) at 0° C. in THF (3 mL) is added phenyllithium (1 mmol). After 30 minutes, aldehyde iii-d⁴ (266 mg, 1 mmol; prepared from isovanillin by the method of Corey, et al, *J Am. Chem. Soc.*, 94:6190 (1972)) in THF (1 mL) is added and the resulting solution stirred for 4 h while warming to room temperature. Methanol (1 mL) is added and the resulting mixture is concentrated. The residue is passed through a plug of silica eluting with hexanes and ether. Concentration of the filtrate yields the desired product.

9.4 Preparation of aniline iii-d⁶

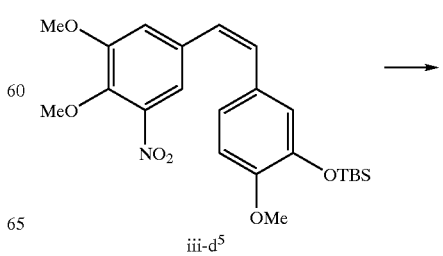

-continued

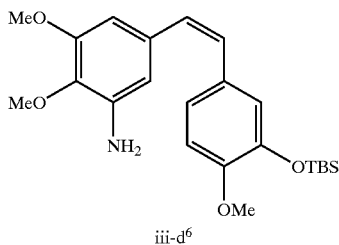
iii-d⁶

To a solution of iii-d⁵ (445 mg, 1 mmol) in ethanol (3 mL) is added tin (II) chloride (379 mg, 2 mmol) and the mixture is heated to reflux until no starting material is present as determined by TLC analysis. The reaction mixture is concentrated and the residue diluted with the ethyl acetate and washed with the saturated NaHCO₃. Drying (MgSO₄) of the organic layer followed by concentration and purification by column chromatography provides the desired product.

9.5 Preparation of sulfonamide iii-d⁷

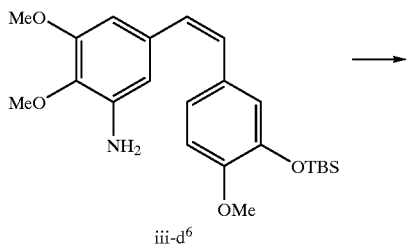
iii-d⁶

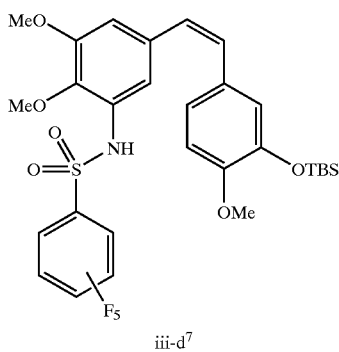
iii-d⁷

A solution of amine iii-d⁶ (415 mg, 1 mmol) and 2,6-lutidene (110 mg, 1.05 mmol) in acetone (3 mL) is treated with pentafluorophenylsulfonyl chloride (0.28 g, 1.05 mmol) while the reaction flask is cooled on an ice bath. The reaction mixture is allowed to warm to room temperature and stirred until TLC shows no starting material remains. The reaction mixture is filtered, concentrated and the residue purified by column chromatography (silica gel; hexanes:EtOAc) to obtain the desired product.

9.6 Synthesis of phenol iii-d

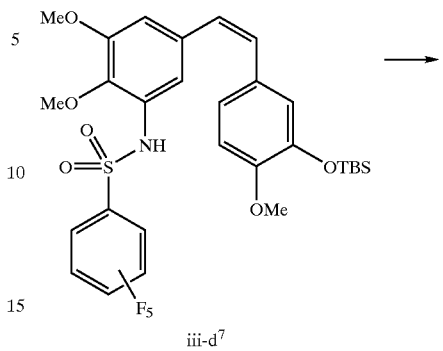
iii-d⁷

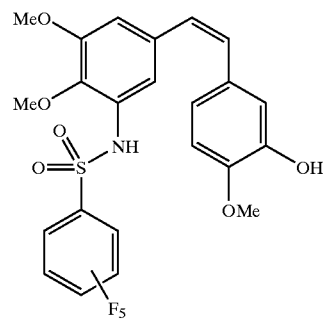
iii-d

Silyl ether iii-d⁷ (645 mg, 1 mmol) is dissolved in THF (1 mL) and cooled to 0° C. Tetrabutylammonium fluoride (1 mL of 1 M solution in THF, 1 mmol) is added and the mixture stirred at 0° C. until no starting material is present as determined by TLC. The reaction mixture is poured onto water, extracted with ether and the ether extracts are dried over MgSO₄. Concentration of the extract followed by chromatography (silica gel; hexanes:EtOAc) of the residue gives the desired product.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A tubulin binding agent that selectively and covalently binds to tubulin, said agent being a derivative of a compound which non-covalently binds to the colchicine binding site, the vinca alkaloid binding site, or the rhizoxin/maytansine binding site of tubulin, said agent selected from the group consisting of:

37
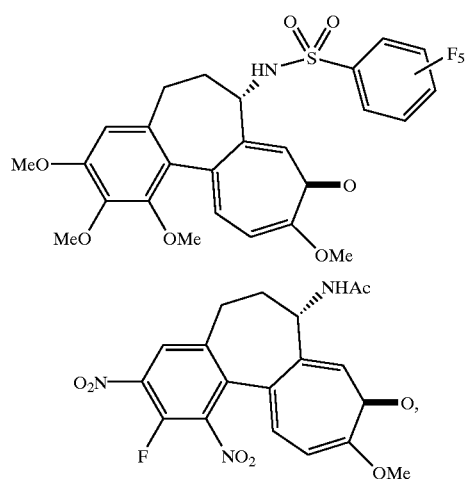
38
-continued
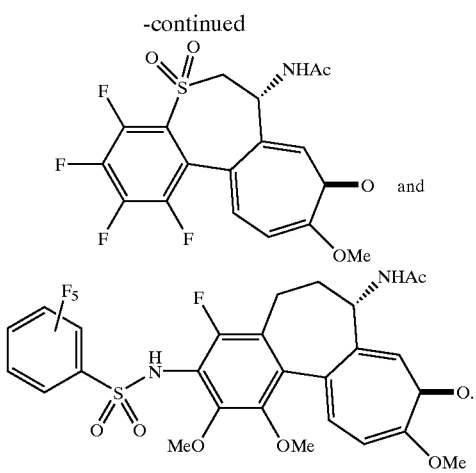
* * * * *